United States Patent [19]

Perali et al.

[11] Patent Number: 4,914,762
[45] Date of Patent: Apr. 10, 1990

[54] INFLATABLE CUSHION

[76] Inventors: Luigi Perali; Costanza Perali, both of Largo Marzabotto 27, 37100 Verona, Italy

[21] Appl. No.: 239,737

[22] Filed: Sep. 2, 1988

[30] Foreign Application Priority Data

Sep. 11, 1987 [IT] Italy .................. 63298/87[U]

[51] Int. Cl.⁴ .............................................. A47C 27/08
[52] U.S. Cl. ............................................. 5/449; 5/432
[58] Field of Search ............... 5/431, 432, 433, 434, 5/436, 441, 449

[56] References Cited

U.S. PATENT DOCUMENTS

| D. 185,477 | 6/1959 | Wuollett | 5/434 X |
|---|---|---|---|
| 2,314,080 | 3/1943 | Dine et al. | 5/431 |
| 2,522,120 | 9/1950 | Kaskey et al. | 5/436 X |
| 2,612,645 | 10/1952 | Boland | 5/441 |
| 3,109,182 | 11/1963 | Doak | 5/434 |
| 3,361,471 | 1/1968 | Radford | 5/432 X |
| 3,426,372 | 2/1969 | Enelow | 5/434 |
| 4,405,129 | 9/1983 | Stuckey | 5/441 X |
| 4,459,714 | 7/1984 | Lin | 5/441 |
| 4,754,511 | 7/1988 | Sargent | 5/449 |

FOREIGN PATENT DOCUMENTS 1314885 12/1963 France .................. 5/434

Primary Examiner—Gary L. Smith
Assistant Examiner—Michael J. Milano
Attorney, Agent, or Firm—Guido Modiano; Albert Josif

[57] ABSTRACT

The inflatable cushion includes a front and rear cloths or flexible sheets having a substantially trapezoidal outline, a peripheral band arranged between and tightly sealed to the front and rear cloths to delimit therewith a sealed enclosure, and a valve means or opening for controllably supplying a fluid to, and discharging it from, the enclosure.

4 Claims, 2 Drawing Sheets

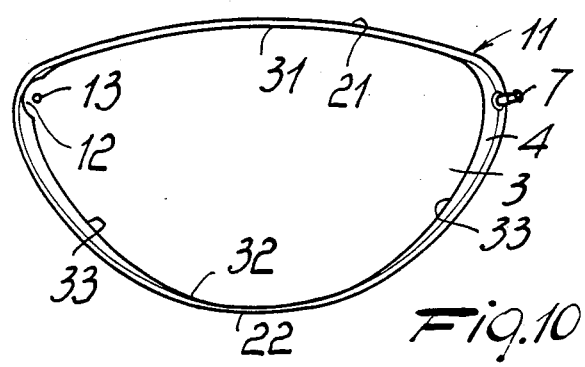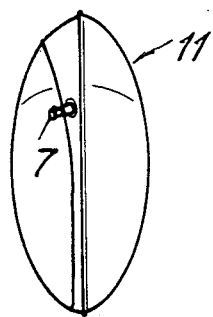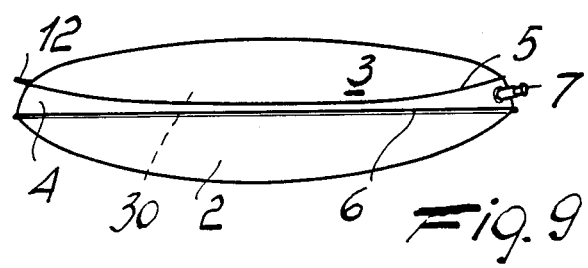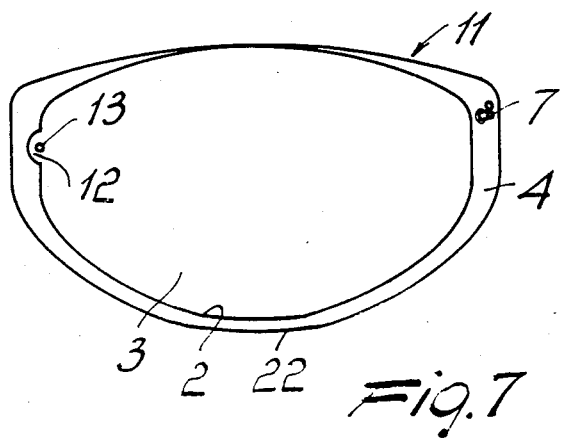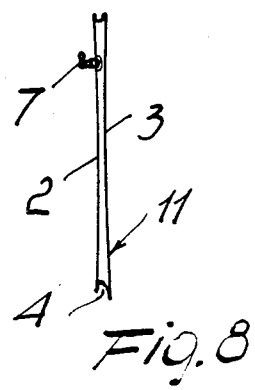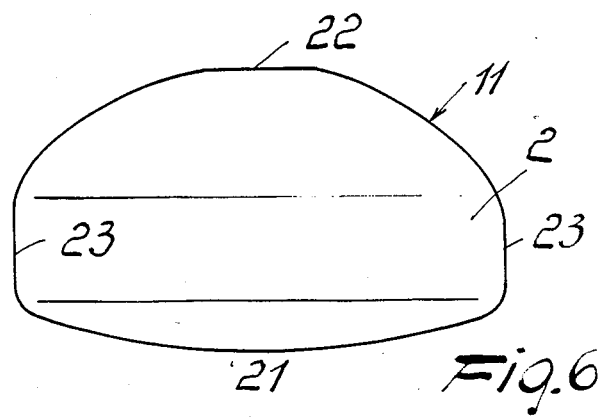

4,914,762

INFLATABLE CUSHION

BACKGROUND OF THE INVENTION

This invention relates to an inflatable cushion. As it is known there are additional inflatable cushions suitable for beds or seats, said cushions being arranged so as to improve the sitting comfort of certain body members.

Some known solutions such as French Patent FR-1,314,885 are showing inflatable cushions having a front and a rear cloth, which are made of strip like elements. Such an arrangement is offering a confortable position to the lower members, as the cushion is having a triangular shape. However, the proposed solution is anatomically not matching the lumbar region of the spinal column and does not provide for a confortable position of the spinal column.

Further, the triangular shape of know cushion is not allowing the assembly of several cushion elements to form a confortable mattress.

Furthermore, the said solution is not sturdy enough, since the rear and the front parts of said cushion are made of bonded strip like elements.

SUMMARY OF THE INVENTION

Therefore it is an object of the present invention to provide an inflatable cushion particularly suitable for use on seats and couches to support and keep the user's trunk well erect in a vertical position with respect to the thighs, thereby making prolonged session in seated or supine position more comfortable and thus assisting in preventing, alleviating or healing lumbagoes of any aetiology.

Another object of the present invention is to provide an inflatable cushion suitable for being used as a pillow or to form a "mattress" for sanitary or hospital purposes.

Another object of the present invention is to provide an inflatable cushion which can act as a hot-water bottle.

A further object of the present invention is to provide an inflatable and reliable cushion of light weight that can be manufactured at relatively low costs.

These and other objects which will better appear below are attained by an inflatable cushion, according to the invention, comprising a front and rear cloth or flexible sheet having a substantially trapezoidal outline, a peripheral band arranged between and tightly sealed to the said front and rear cloths to delimit therewith a sealed enclosure, and valve means for controllably supplying a fluid to, and discharging it from, said enclosure.

BRIEF DESCRIPTION OF THE DRAWINGS

Further features and advantages are illustrated in the following description of some presently preferred embodiments of an inflatable cushion, given by way of non-limiting examples with reference to the accompanying drawings, in which:

FIG. 6 is an elevational view of another embodiment of the cushion according to the invention;

FIG. 7 is a rear view of the cushion of FIG. 6 in a deflated condition;

FIG. 8 is a side view of the cushion of FIG. 7;

FIG. 9 is a view from below of the cushion of FIG. 7 in an inflated condition;

FIG. 10 is a view from above of the cushion of FIG. 9;

FIG. 11 is a side view of the cushion of FIG. 10, and

FIG. 12 shows a way of using a cushion according to the invention.

DESCRIPTION OF THE PREFERRED EMBODIMENTS

Figure 5:
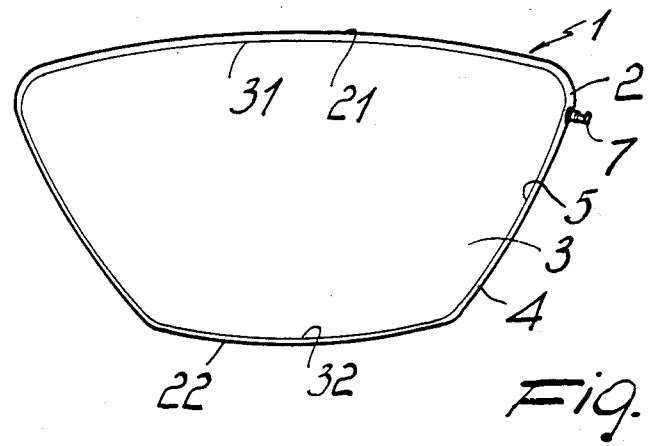
FIG. 5 is a plan view of the cushion of FIG. 4.

In the Figures of the accompanying drawings the same reference numerals have been used to indicate the same or similar parts or components.

Figure 4:
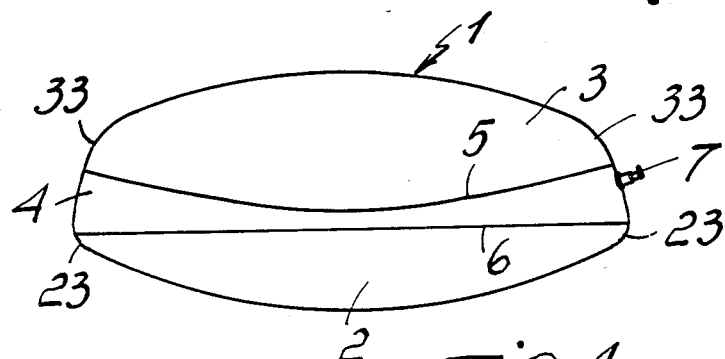
FIG. 4 is a view from below on an enlarged scale of the cushion of FIG. 1.
Figure 1:
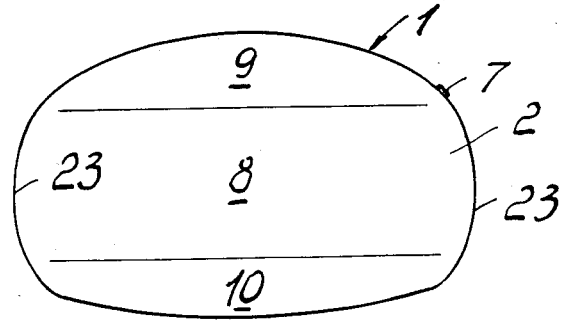
FIG. 1 is an elevational front view of an inflatable cushion according to the invention.
Figure 2:
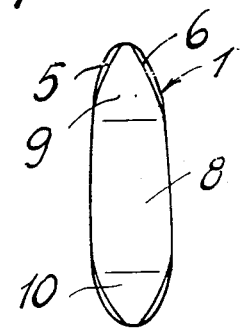
FIG. 2 is a side view of the cushion of FIG. 1.
Figure 3:
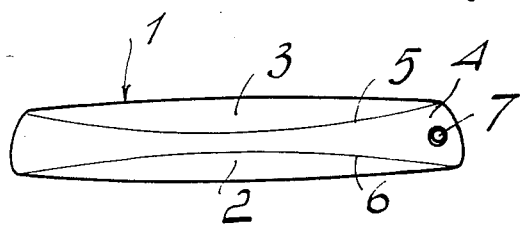
FIG. 3 is a view form above of the cushion of FIG. 1.

With reference first to the embodiment shown in FIGS. 1 to 5, an inflatable cushion 1 comprises four main components, namely a front cloth 2, a rear cloth 3, a peripheral band 4 and an inlet-outlet valve or opening 7. The cloths or flexible sheets 2 and 3 are made advantageously of a flexible, washable, airtight and waterproof material, e.g. rubberized canvas, whereas the band 4 can consist of a thermoplastic sheet material, such as PVC (polyvinyl chloride), polyethylene and the like, or rubber. The band 4 is sealed both along its side edges 5, 6 to respective edges of the cloths 2 and 3 by way of any suitable sealing technique, e.g. by using a sealing agent or by heat sealing, and along its front edges (not shown), thereby forming a tight loop surrounding the cloths 2 and 3 and delimiting therewith an inner waterproof and airtight enclosure 30. Thus, the cushion 1 can be inflated either by blowing in it a gaseous fluid, such as air, or by filling it with a liquid, e.g. water.

The supply to, and the discharge from, the enclosure 30 of a fluid can be controlled by the valve 7 which can be of any suitable design easily available on the market, e.g. a valve commonly used on water or inflatable mattresses, so that the cushion can be inflated and deflated to a desired extent.

More particularly, the cloths 2 and 3 have a substantially trapezoidal outline with the cloth 2 having a lower or major base 21 an upper or smaller base 22 and sides 23 and the cloth 3 having a lower or major base 31, an upper or smaller base 32 and sides 33.

Advantageously, the rear cloth or sheet 3 is smaller in size that the front cloth or sheet 2 so that, in use, it is kept well hidden behind the front cloth, whereas the peripheral band 4 can take a slanting configuration with respect to the front cloth. Thus, in its inflated or erected condition, the cushion, has a substantially truncated-pyramid configuration, said front cloth 2 defining the major base of the trucated-pyramid, said rear cloth 3 defining the minor base of the truncated-pyramid and said band 4 defining the lateral surface thereof. Such a configuration is advantageous for locating the cushion on a seat or couch (e.g. chairs, car seats, beds, cots, folding beds and the like) since the cushion adjusts itself to the concavity of the seat or seat back and remains substantially stationary in it.

Moreover, the peripheral band 4 can be so designed as to be narrower at two lenghts thereof corresponding to the major and smaller bases of the clothes 2 and 3. Accordingly, when properly inflated, a cushion 1 takes a biconvex lens-like configuration, where three distinct transverse areas or portions at different levels can be identified, i.e. an intermediate wider area 8 arranged to anatomically match with the lumbar portion of the user and an upper and a lower area 9 and 10, respectively, which grow thinner from the intermediate area 8 outwards.

More particularly the upper area 9 is designed to provide a comfortable support for the user's back, e.g. when in a seated position, to keep his backbone in a substantially straight (vertical) position, whereas the lower area 10 can act as a bearing portion for the cushion.

This feature makes the cushion specifically anatomically suitable for use at the lumbar or cervical region (lordosis) of the spinal column (backbone).

When inflated to a lower extent the cushion 1 can have its two faces 2 and 3 arranged substantially parallel to one another, in which case the cushion can be advantageously used as a pillow or a small mattress.

FIGS. 6 to 11 show a cushion 11 which is similar to cushion 1 and is also constituted by front and rear cloths 2 and 3, peripheral band 4 which acts as a bridging component between cloths 2 and 3 and a valve or opening 7, preferably seated on the band 4. Advantageously the cloth 3 has a tab 12 formed with a hole 13 for hanging up the cushion 11.

The cushions 1 and 11 are specifically meant for taking and keeping a correct seated position which is achieved when the trunk is well erect along a vertical line with respect to the thighs. In such a position, the user's agonists and antagonists muscles responsible for keeping the spinal column erect do work in a balanced condition with minimum expenditure of energy, and thus the seated position can be endured for longer periods without fatigue (simple lumbalgy). Moreover, in the erect position the vertebral bodies are kept mutually parallel one above the other, thereby exerting a uniform pressure on the various intervertebral disks which are thus held in position. It is a known fact that backward opening of intervertebral spaces which occurs when the spinal column is bent forwards, assists the movement of the core when splits occur in the gelatinous disk and/or upon breakage of the anulus fibrosus surrounding the disk (generally speaking this occurs owing to a trauma). Migration of the core inside the disk is responsible for a series of disorders and symptoms which in the less severe cases are termed lumbalgies which, although being relatively benign and temporary diseases, are nonetheless invalidating. In the most serious cases the core can comprss the proximate nerve roots, which results in a paresis and in sharp pain (e.g. sciatalgias). Such painful diseases require an operation for being cured. Both situations get substantial benefit from restoration and preservation of the correct positioning of the vertebral bodies, and this can be achieved by using a cushion according to the present invention, e.g. as shown in Figure 12.

If a plurality of cushions 1, 11 are filled with water and used as a mattress, they can constitute a useful means against the formation of bedsores which are produced on the most vulnerable parts of the body of patients in badly deteriorated general conditions and suffering from such a disease affecting coxofemural articulations, sacrum, gluaei, heels etc.

The advantageous features of a cushion according to the invention with respect to water mattresses known in the art are that The cushion, being a small unit, can be easily handled, arranged and located by a single operator or the patient himself;

Two or four cushions can be assembled to form a mattress;

A single cushion can be located under limited areas of the patient's body, such as a heel, an elbow, etc.

Its manufacturing cost is quite low and competitive in any case; and

It can also be filled with hot water to act as a hot-water bottle.

I claim:

1. An inflatable cushion having:
    a front larger cloth and a rear narrower cloth each having a major and a smaller base and two sides which define a substatially trapezoidal border outline,
    an intermediate band extending between, and tightly sealed to, the borders of said front cloth and rear cloth to delimit therewith a sealed enclosure for a fluid, said band having a narrower width along said major and said smaller base and a larger width along the two sides of said flexible sheets,
    and a check valve means for supplying a fluid to said enclosures, to erect the cushion to a biconvex lens-like configuration where it comprises an intermediate wider transverse portion and an upper portion and a lower portion growing thiner from the intermediate portion outwards.

2. An inflatable cushion as claimed in claim 1 wherein, in its inflated condition, it takes a substantially truncated-pyramid configuration, said front cloth defining the major base of the truncated-pyramid, said rear cloth defining the minor base of the truncated-pyramid and said band defining the lateral surface thereof.

3. An inflatable cushion as claimed in claim 1 wherein, in its lesser inflated condition, said front said said rear cloth are substantially parallel to one other.

4. An inflatable cushion as claimed in claim 3 wherein, at least two cushions in said lesser inflated condition are assembled to form a mattress.

* * * * *